United States Patent
Lee et al.

(10) Patent No.: US 10,130,754 B2
(45) Date of Patent: Nov. 20, 2018

(54) MODULAR MEDICAL PUMP SYSTEM

(71) Applicant: Zyno Medical, LLC., Natick, MA (US)

(72) Inventors: Chao Young Lee, Weston, MA (US); Mei Zhang, Sharon, MA (US)

(73) Assignee: Zyno Medical, LLC, Natick, MA (US)

( * ) Notice: Subject to any disclaimer, the term of this patent is extended or adjusted under 35 U.S.C. 154(b) by 125 days.

(21) Appl. No.: 14/939,349

(22) Filed: Nov. 12, 2015

(65) Prior Publication Data

US 2017/0136177 A1   May 18, 2017

(51) Int. Cl.
*A61M 5/14*   (2006.01)
*A61M 5/172*   (2006.01)
*A61M 5/145*   (2006.01)
*A61M 5/168*   (2006.01)
*A61M 5/142*   (2006.01)

(52) U.S. Cl.
CPC ........ *A61M 5/1413* (2013.01); *A61M 5/1452* (2013.01); *A61M 5/14228* (2013.01); *A61M 5/16813* (2013.01); *A61M 5/16831* (2013.01); *A61M 5/172* (2013.01); *A61M 2205/3334* (2013.01); *A61M 2205/3553* (2013.01); *A61M 2205/502* (2013.01); *A61M 2205/6009* (2013.01); *A61M 2205/6081* (2013.01); *A61M 2205/82* (2013.01); *A61M 2209/082* (2013.01)

(58) Field of Classification Search
CPC ...... A61M 5/16827; A61M 2205/6009; A61M 2205/8256; A61M 5/50; A61M 5/5086
See application file for complete search history.

(56) References Cited

U.S. PATENT DOCUMENTS

| | | | |
|---|---|---|---|
| 4,512,764 A | 4/1985 | Wunsch | |
| 4,513,796 A | 4/1985 | Miller et al. | |
| 4,559,036 A | 12/1985 | Wunsch | |
| 4,637,817 A | 1/1987 | Archibald et al. | |
| 4,681,563 A | 7/1987 | Deckert et al. | |
| 4,925,444 A | 5/1990 | Orkin et al. | |
| 4,966,579 A | 10/1990 | Polaschegg | |
| 5,318,546 A | 6/1994 | Bierman | |
| 5,782,805 A * | 7/1998 | Meinzer | A61M 5/172 604/131 |
| 6,017,318 A | 1/2000 | Gauthier et al. | |
| 6,241,704 B1 * | 6/2001 | Peterson | A61M 5/14228 604/31 |
| 7,802,569 B2 | 9/2010 | Yeates et al. | |
| 8,672,875 B2 * | 3/2014 | Vanderveen | A61M 5/16827 137/109 |
| 9,106,083 B2 * | 8/2015 | Partovi | H02J 7/025 |
| 2005/0277873 A1 * | 12/2005 | Stewart | A61M 5/14 604/93.01 |
| 2010/0121170 A1 * | 5/2010 | Rule | A61B 5/1427 600/365 |

(Continued)

*Primary Examiner* — Laura Bouchelle
*Assistant Examiner* — Tasnim M Ahmed
(74) *Attorney, Agent, or Firm* — Boyle Fredrickson S.C.

(57) ABSTRACT

A modular medical pump system provides separate pump units that may be pre-associated with flexible tubes. Multiple pump units may be installed in a controller that coordinates operation of the pump units for delivery of multiple medicaments to a patient. The pump units may carry drug information and the controller may hold patient information allowing drug delivery and interaction to be assessed by the controller.

23 Claims, 6 Drawing Sheets

(56) References Cited

U.S. PATENT DOCUMENTS

| | | | | |
|---|---|---|---|---|
| 2012/0078218 A1* | 3/2012 | Barnes | ............... | A61M 5/1413 |
| | | | | 604/500 |
| 2012/0179130 A1* | 7/2012 | Barnes | ............... | G06F 19/00 |
| | | | | 604/500 |
| 2012/0316435 A1* | 12/2012 | Burg | ............... | A61M 5/14212 |
| | | | | 600/432 |
| 2013/0208497 A1* | 8/2013 | Provost | ............... | A61M 5/14 |
| | | | | 362/555 |
| 2014/0243749 A1* | 8/2014 | Edwards | ............... | A61M 5/31 |
| | | | | 604/187 |
| 2015/0379237 A1* | 12/2015 | Mills | ............... | G06F 19/3468 |
| | | | | 705/2 |

* cited by examiner

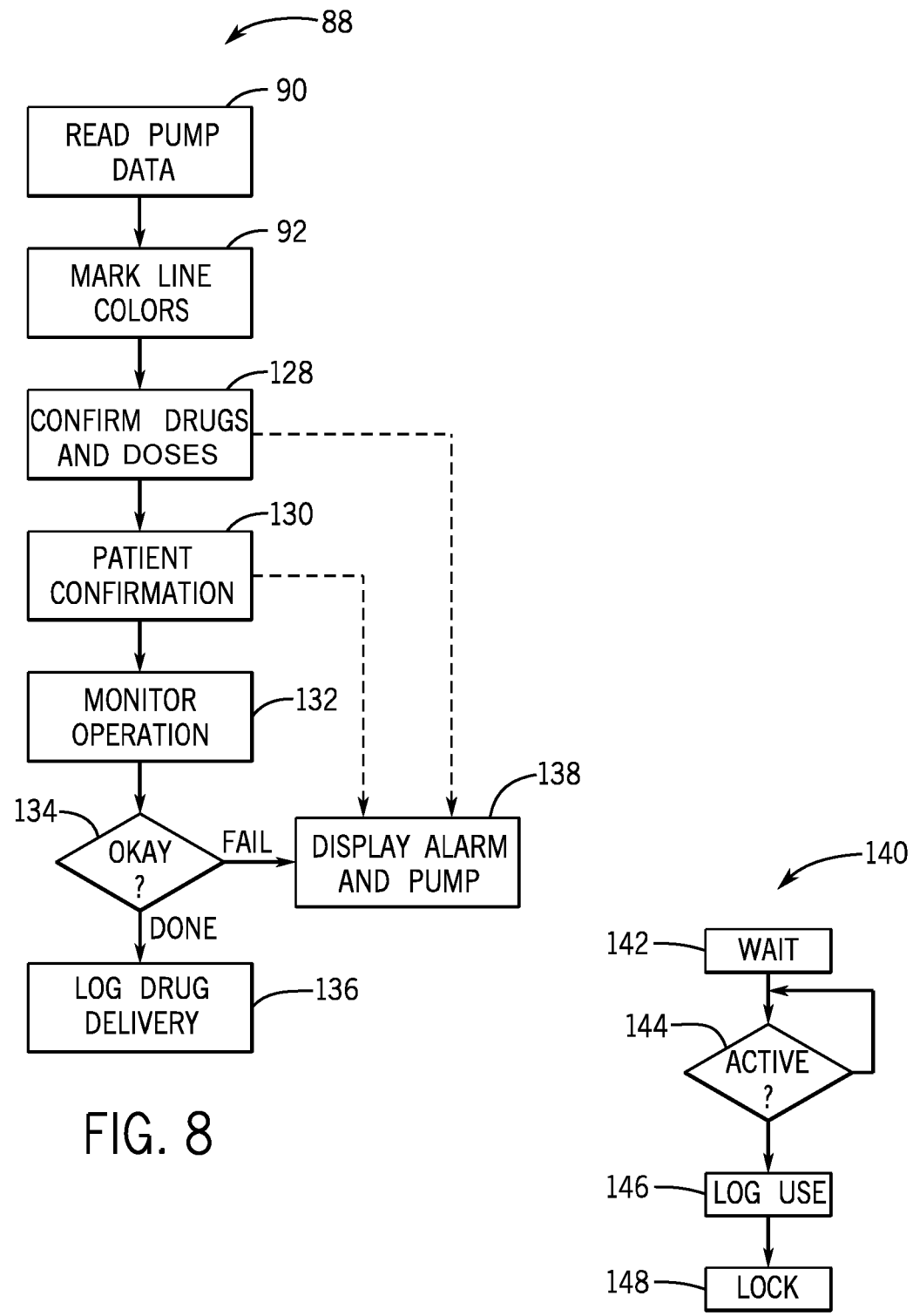

MODULAR MEDICAL PUMP SYSTEM

BACKGROUND OF THE INVENTION

Medical pumps, such as syringe pumps or peristaltic infusion pumps, are known for computer-controlled delivery of medication as well as hydration and nutrition agents (henceforth medicaments) to patients over a period of time. Typically the medicament is at in a syringe (for a syringe pump) or a flexible bag or a bottle (for peristaltic infusion pump, or ambulatory pump) that may be connected to a flexible tube and attached to a needle inserted into the patient.

When a healthcare professional ministering to the patient receives the medicament, the healthcare professional reviews the medicament description for correctness and enters the desired dose and rate into the pump. Other pump parameters such as alarm limits and the like may also be programmed into the pump at this time. The syringe or flexible tube must then be mechanically connected to the pump mechanism, the needle introduced into the patient, and the mechanism activated to begin pumping.

Current medical pumps can be costly driven in part by the need for long-lived mechanical components and a desire to avoid costly servicing. The operating costs of current medical pumps are also high because of the complexity attendant to having attending nurses or healthcare professionals program the pumps for the proper dosage for the patient and according to the particular drug.

Often a patient will need multiple simultaneous or sequential medicament deliveries involving, for example, multiple syringes, multiple bags and multiple pumps. The process of collecting the necessary pumps near the patient, installing the syringes, flexible tubes and bags, and properly programming the different pumps can be time-consuming and difficult even for skilled practitioners. The existence of multiple medicaments also greatly increases the possibility of confusing medicaments by installing them in the wrong pumps, programming the different pumps incorrectly, or even confusing the flexible tubes and their locations. When multiple medicaments are introduced to a patient, the risk of adverse interactions between drugs must be assessed by the healthcare professional. This may not always occur if different personnel are responsible for different medicaments and the medicaments are provided at different times.

SUMMARY OF THE INVENTION

The present invention provides a modular pump in which the mechanical elements are segregated into a first pump unit that can be readily replaced independent of a control unit providing more expensive and long-lived elements. This modularity allows regular replacement of the pump module permitting highly cost-effective components to be used in the pump unit. Providing a low-cost and modular pump unit also allows the pump unit to be pre-attached to a drug kit of an IV line in a drug container (for example, by the dispensing pharmacist or the like) and thereby to serve as a vehicle for communicating drug information and dosage.

In one embodiment the controller may provide for multiple receptacles receiving low-cost pump units which may be simply plugged into the controller to simplify the delivery of multiple medicaments simultaneously or in sequence. The controller may provide for shared resources such as a display as well as more costly components such as line sensors, wireless communication, and the like, again, greatly reducing the incremental cost of the pump units.

In one embodiment, the invention provides a modular medical pump system for a drug kit of a type having a flexible delivery tube from a drug container. The modular medical pump includes a controller with (a) an electronic processor holding a first stored program for execution by the electronic processor; and (b) a programming station interface for releasably receiving a pump unit for communication of control information to the pump unit as so received based on the execution of the first stored program. The modular medical pump system further includes at least one pump unit releasably receivable by a connector of the controller, the one pump unit including: (a) a housing for receiving the delivery tube therethrough, the housing including a retention element locking at least one of the delivery tube and a drug container to the housing of the pump unit against unauthorized removal; (b) an electromechanical pump communicating with a flexible tube in the housing to pump fluid through the flexible tube; (c) a pump unit electronic processor communicating with the electromechanical pump and holding a stored program; and (d) a pump unit interface for receiving the control information from the controller for control of the electromechanical pump when the pump unit is received by the controller.

It is thus a feature of at least one embodiment of the invention to provide a "bare-bones" pump unit that is easily replaceable so as not to limit the practical life of the pump system and to allow pump units to be pre-attached to drug kits to track, monitor, and control the lifecycle of the drug in a medical environment.

The drug container may remain external to the housing.

It is thus a feature of at least one embodiment of the invention to minimize pump unit costs through the use of a housing that cannot contain the drug container.

The pump unit maybe sized and adapted to be fully supported on the drug kit when the drug kit is transported.

It is thus a feature of at least one embodiment of the invention to permit the pump unit to be pre-attached to the drug kit and transported therewith to the patient side.

The retention may require an unlocking tool to remove the drug kit from the housing and/or may provide a tamper feature indicating attempted unauthorized removal of the drug kit from the housing.

It is thus a feature of at least one embodiment of the invention to ensure integrity in allowing the pump unit to track, monitor, and control the lifecycle of a drug.

The controller may further provide a source of electrical power to the pump unit when the pump unit is received by the controller.

It is thus a feature of at least one, embodiment of the invention to minimize power storage in the pump unit to reduce its cost and weight.

The controller may further include a wireless transceiver for communicating with a remote medical database and/or include guides for receiving the delivery tube and wherein the guides include proximate sensors for sensing at least one of: a flow rate through the flexible tube, air bubbles in the flexible tube, and a pressure in the flexible tube.

It is thus a feature of at least one embodiment of the invention to allow the controller to provide long-lived elements needed for a medical pump eliminating the need to associate those with the pump unit.

Each pump unit may include a mechanical flexible tube clamp closing the flexible tube against flow that is released when the pump unit is received by the controller.

It is thus a feature of at least one embodiment of the invention to allow pre-attachment of the pump unit to the drug kit without risk of drug leakage or loss before the pump system is fully assembled.

The pump unit may be exclusive of manually operated controls activating the pump unit.

It is thus a feature of at least one embodiment of the invention to minimize the cost and weight of the pump unit.

The pump unit may include a syringe-engaging structure for holding a syringe and preventing non-damaging manual removal of the syringe from the pump unit after it is attached without use of an unlocking tool.

It is thus a feature of at least, one embodiment of the invention to provide a lightweight pump unit that can deliver medicaments normally requiring a syringe pump.

In one embodiment the controller may include multiple connectors for releasably receiving multiple pump units, each connector providing a receptacle for receiving and supporting the housing of the pump unit.

It is thus a feature of at least one embodiment of the invention to leverage shared components and circuitry (for example, a keyboard, display, wireless communication circuitry and power processing circuitry) when multiple drugs are being delivered by providing those components and circuitry in the control unit to be shared among multiple pump units.

The housing of the pump units may include a replaceable drug identification indicium.

It is thus a feature of the invention to reduce the chance of confusion in administering drugs by pre-labeling the pump units with the drug identification, for example, at the time of dispensing of the drug.

The controller may include mountings holding the controller on an IV pole.

It is thus a feature of at least one embodiment of the invention to provide a form factor familiar to hospitals and the like in which a pump system may be installed bedside.

The modular medical pump may provide a human-perceivable indicium unique to and proximate to each flexible tube of an associated installed pump unit marking the flexible tubes for a separate identification and these human-perceivable indicia maybe electronically controlled to be changed according to the pump units installed in the controller.

It is thus a feature of at least one embodiment of the invention to permit a shared resource such as a screen or keyboard to be instantly identified to a particular drug delivery tube to reduce confusion when multiple drugs are being delivered.

The human-perceivable indicia may provide an illumination of the flexible tube according to the pump units installed in the controller.

It is thus a feature of at least one embodiment of the invention to provide a simple and clear marking of drug delivery tubes that can be implemented in the controller without pre-marking of the drug kit.

These particular objects and, advantages may apply to only some embodiments falling within the claims and thus do not define the scope of the invention.

BRIEF DESCRIPTION OF THE FIGURES

FIG. 8 is a flowchart of the program steps implemented by the base station during pumping;

FIG. 9 is a flowchart of the principal steps executed by the pump module during pumping;

DETAILED DESCRIPTION OF THE PREFERRED EMBODIMENT

Figure 1:
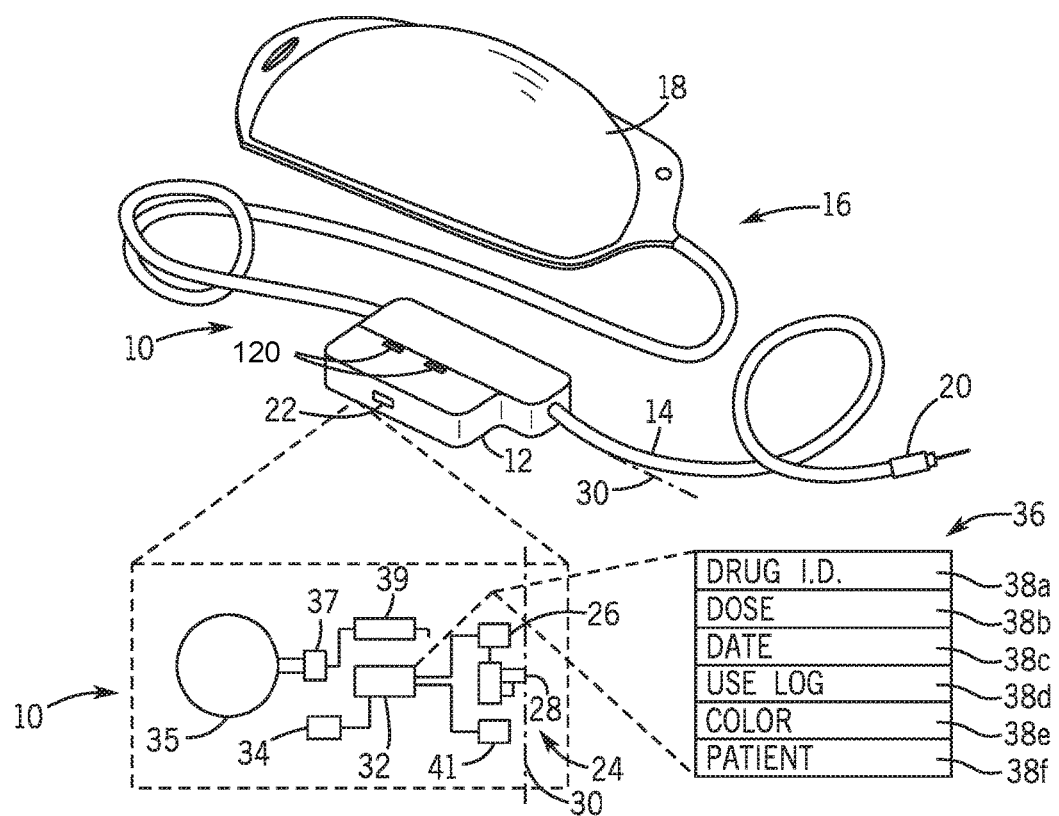
FIG. 1 is a perspective view of a pump unit installed on an IV bag and showing a block diagram of the elements of the pump unit and data that may be held by the pump unit.
Figure 10:
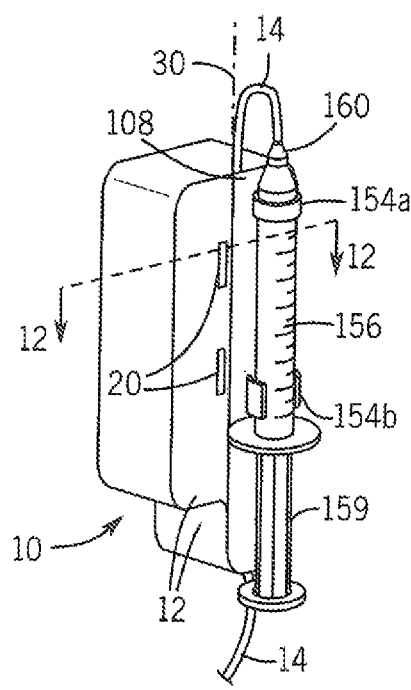
FIG. 10 is a perspective view of a pump unit having mounting clips on the housing for supporting a syringe holding a medicament.

Referring now to FIG. 1, the present invention may provide multiple pump modules 10 each having a compact housing 12 that may be installed around an flexible tube 14 on drug kit 16, the latter also including a medicament bag 18 and needle attachment luer 20 or in some embodiments flexible tube 14 and syringe 156 (shown in FIG. 10).

As will be discussed below, the attachment of the housing 12 around the flexible tube 14 may be tamper-resistant requiring a special tool to be inserted through release openings 120 for the release of the flexible tube. The housing 12 may also include retention features, for example, notches 22 that will be used to hold the housing 12 into a base station 44 to be described and shown in FIG. 2.

Generally, the pump modules 10 have a minimized complexity, including in the minimum configuration a pump actuator 24 including a pump motor 26 such as an electric DC motor communicating with a peristaltic pump mechanism 28. The pump mechanism 28 may have fingers that can pump fluid peristaltically through the flexible tube 14 as positioned on axis 30 adjacent to the pump mechanism 28. The pump motor 26 communicates with a microcontroller 32 holding simple operating program that permits the microcontroller 32 to communicate with a communication interface 34 to receive commands and instructions from the base station to be described and to transmit data such as drug data to the base station. This communication interface 34 may be a near field communication interface employing a radio communication protocol, or employing optical communication or a direct electrical connection through a releasable electrical connector. In some embodiments the communication interface may employ data sent through the wireless power transmission coils 35 to be described below with respect to FIG. 3.

As noted, the pump modules 10 may include a wireless charging coil 35 for receiving electrical power sufficient for fully powering the microcontroller 32 and the motor 26. The wireless charging coil 35 receives power through power control circuit 37 in the manner conforming to any of a number of wireless charging standards including, for example, those of the A4WP (Alliance for Wireless Power), PMA (Power Matters Alliance) or (WPC) Wireless Power Consortium, such standards generally available to the public and hereby incorporated by reference. The power control circuit 37 may also be associated with a temporary storage element 39 such as a super capacitor or rechargeable battery providing power smoothing. Alternatively, direct electrical connections may communicate power and data between the pump modules 10 and the base station 44.

Optionally the pump module 10 may incorporate one or more line sensors 41 which may detect any of pressure, flow rate, or bubbles in the flexible tube 14 placed along axis 30.

The microcontroller 32 may include programmable memory 36 that may hold information 38 about the medicament in the medicament bag 18 including medicament information 38*a* (such as a drug name or identification number). Optionally, the memory 36 may also hold a desired dose information 38*b* indicating the amount, flow rate, and timing of the drug delivery, expiration date information 38*c* limiting use of the medicament bag 18 to within a date range, use-log information 38*d* that may be used to record operation of the pump in delivering the medicament, pump color information 38*e* related to identifying the pump and the flexible tube 14 during use and the patient identification information 38*f*. In a simple embodiment, only the medicament information 38*a* is provided allowing the drug kit 16 to be pro-stocked for use with any patient. A more sophisticated approach allows for the programming of any or all of the additional information described above. In one embodiment, the pump module 10 fully supports itself on the drug kit, for example, and is clamped to the flexible tube 14 or attached but does not contain the medicament bag 18 by mechanical means so that they may be shipped together without damage or separation. In this regard the weight of the medicament bag 18 will be less than a pound, a weight value difficult to obtain with a full-featured pump system.

Figure 2:
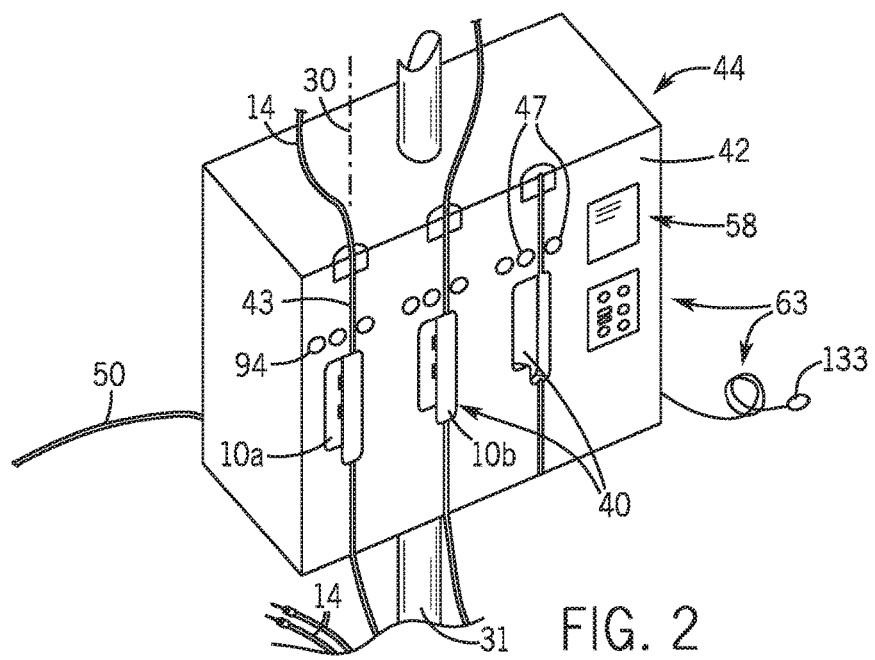
FIG. 2 is a perspective view of two pump units installed in a base station having multiple receptacles for receiving the pump units and the flexible tubes to which they are attached.

Referring now to FIG. 2, multiple pump modules 10*a*, 10*b* may fit within any of multiple sockets 40 on a front faceplate 42 of the base station 44 after the pump modules 10 have been installed on the flexible tubes 14. The flexible tubes 14 for these pump modules 10*a* and 10*b* may be received by vertical channels 43 in the front faceplate 42 aligned with axis 30 of the pump modules 10 so that the pump modules 10 do not need to be removed from the flexible tubes 14 for this installation. The channels 43 may have retention elements, for example, elastomer collars, that retain the flexible tubes within the channels against unintended dislodgment. By installing multiple pump modules 10 into the base station 44, a patient requiring multiple medicaments can be treated simply by obtaining the appropriate pump modules 10 preinstalled on the drug kit 16 and inserting the necessary pump modules 10 into any open socket 40. In this embodiment, the base station 44 may mount on an IV pole 31 for familiar integration into the medical environment and to hold the medicament bag 18.

Figure 3:
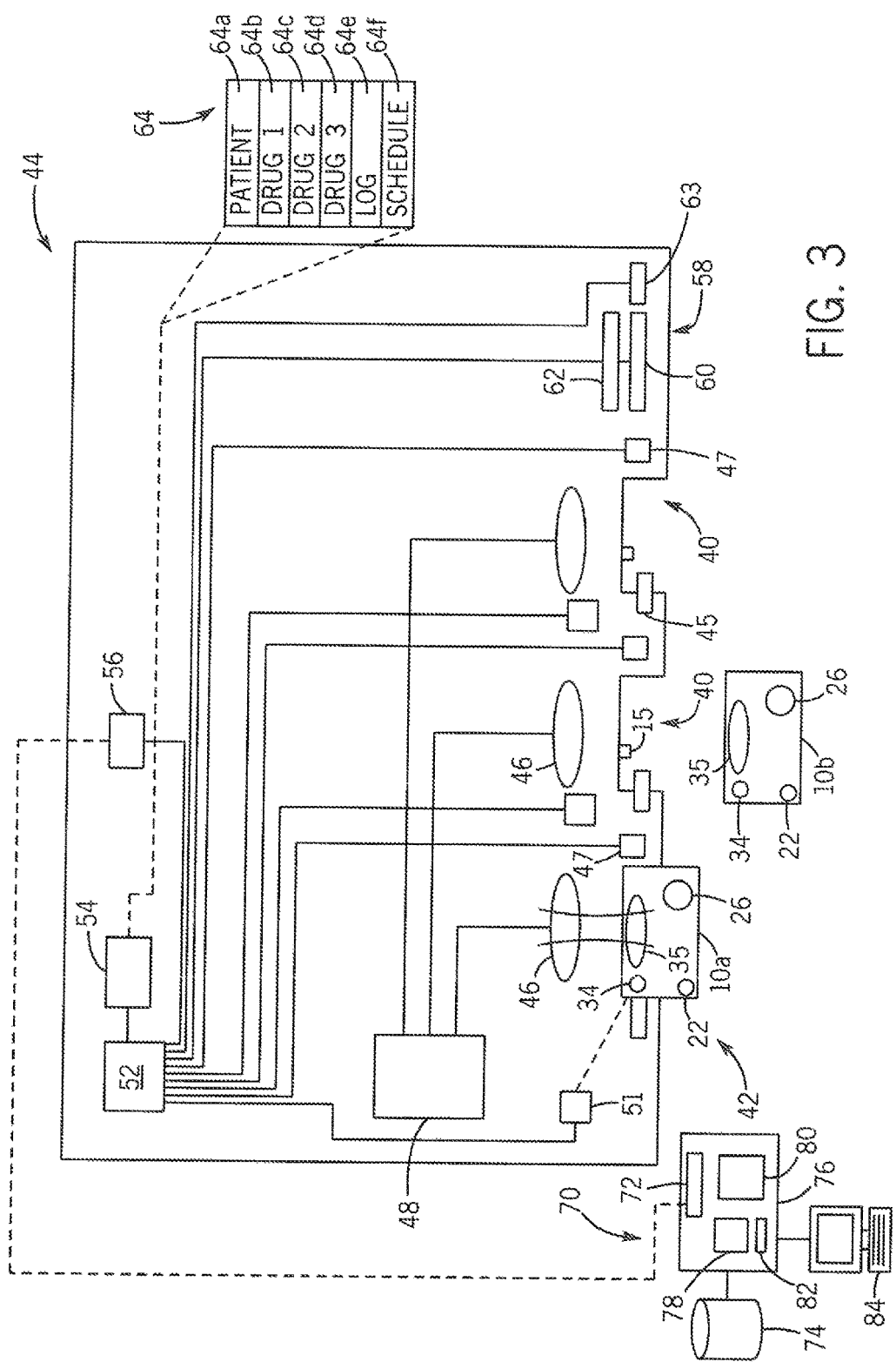
FIG. 3 is a block diagram of the elements of the base station showing pump units and a communicating electronic medical record system.

Referring now to also to FIG. 3, each of the sockets 40 may provide a spring-loaded pin 45 engaging with the notch 22 in the housing 12 of the pump module 10 to releasably hold the pump modules 10 in the sockets 40 against unintended release. When so positioned, the wireless charging coils 35 of the pump modules 10 may be in close proximity and aligned with corresponding wireless charging coils 46 within the base station 44. This alignment provides a magnetic flux coupling that allows power transfer from the base station 44 to the pump modules 10 in the sockets 40 without exposing the conductors. The coils 46 may be driven by an AC power source 48 receiving power from a line cord 50 (shown in FIG. 2).

The base station 44 may also include flexible tube sensors 47 positioned along the channels 43 (shown in FIG. 2) for sensing flexible tube pressure, bubbles in the IV fluid, and flow rate. Nonlimiting examples of sensors for such systems are described in U.S. patent application Ser. No. 14/104,371 filed Dec. 12, 2013, assigned to the assignee of the present invention, and hereby incorporated by reference. Those sensors can be integrated on the pump if preferred.

When the pump modules 10 are in the sockets 40, the communication interface 34 may communicate with the corresponding interface 51 within the base station 44 proximate to a given socket 40. These communication interfaces 34 and 51 allow for the bidirectional exchange of information and command signals between the base station 44 and the pump modules 10 as will be discussed below.

The base station processor 52 may also communicate with a memory 54 holding stored data and a stored program executable by the base station processor 52. In addition, the base station processor 52 may communicate with a wireless transceiver 56, for example, executing the IEEE 802.11 Wi-Fi standard, as well as a user interface 58 including, for example, a graphics display 60 having a three color backlight 62 as will be described below and with data entry device 63, for example, being a keyboard, a barcode scanner, an RFID tag reader or the like allowing entry of the information by a user proximate to the base station 44.

The memory 54, as well as holding the operating program, may hold patient information 64 including patient identification information 64*a* and identification of each of the medicaments to be received by the patient as medicament information 64*b*, 64*c*, and 64*d*. The memory 54 may also hold a data log for logging actual delivery of medicament to the patient including the amount delivered date and any error codes generated. In addition, the patient information 64 may include a treatment schedule 64*f* providing treatment dosages for different drugs, an order of dosage, a total volume of dosage, and other treatment information.

This patient information 64 may be obtained from a central electronic medical record system 70 communicating with the base station 44 through the wireless transceiver 56 and a corresponding transceiver 72 of the electronic medical record system. As is generally understood in the art, an electronic medical record system may include a database 74 of patient, records including treatment prescriptions managed by electronic computer 76. Electronic computer 76 may have a processor 78, local memory 80, and a network interface 82 communicating with multiple operating terminals 84 for the entry and extraction of information from the electronic medical record system during the normal course of business of a hospital or other health care facility.

Referring now also to FIG. 8, a program 88 held in memory 54 of the base station 44 (shown in FIG. 3) upon activation by an operator, or by detection by the base station processor 52 of the installation of a pump module 10, may read the data from the pump module 10 or a drug container attached to the pump module 10 as indicated by process block 90. At a minimum this information provides the drug identification information 38*a* (shown in FIG. 1) but may include any of the information 38*b*-38*f*.

On the other hand, information about the drug (including but not limited to infusion parameters, treatment schedule, patient name, date of birth and ID, etc.) can be obtained by the base station 44 then communicated to the pump modules 10. Such drug information may be carried by the drug bags/syringes through a data carrier, which can be barcodes, and/or RFID, and/or NFC tag, etc. Information stored in the data carrier can be transferred to the base station then transferred to the pumps. Drug information can also be obtained by the base station 44 through wired or wireless communication with a database 74 then communicated to the pump modules 10. Information in the data carrier can be just an ID for the base station to search database 74 and obtain the drug information. Drug information can also be transferred directly from database 74 to the pump modules 10 through wired or wireless communication. Drug information can also be obtained by the pump modules 10 directly through the data carrier, or through reading the ID from the data carrier and then communicating with either the base station 44 or the database 74 itself.

At process block 92 the base station 44 may assign a color or other visual marking to the pump module 10, for example, by illuminating a colored LED 94 associated with each socket 40 as shown in FIG. 2. A similar color may be used as the background to the display 60 provided by backlight 62 (shown in FIG. 3) during interrogation or programming or activation of the pump module 10 associated with that color. Alternatively, a colorless identification may be adopted, for example, by a flashing of LEDs 94 to signal a correspondence between information on the display 60 and a particular pump module 10 being activated, programmed, or interrogated.

Figure 4:
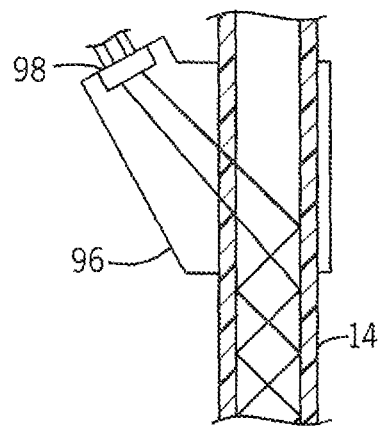
FIG. 4 is a cross-sectional view along an axis of the flexible tube as received in the base station showing an illumination of the flexible tube for identification.

Referring momentarily to FIG. 4, in one embodiment, the invention contemplates that either colored-distinguished illumination or illumination without color distinction may be applied to the flexible tubes 14 as part of this marking process. In particular, the flexible tubes 14 fitting within the channels 43 (shown in FIG. 2) may be received within a channel illuminator 96. A single or three-color LED 98 may be optically coupled to the channel illuminator 96 which surrounds the flexible tube 14 and, by means of internal reflection through the channel illuminator 96 through the walls of the flexible tube 14, may inject light into the walls, and/or lumen of the flexible tube 14 to be conducted in the IV fluid or walls in the manner of a light pipe. This illumination may be coordinated with illumination of the display 60 to also designate the particular pump module 10 being accessed through the user interface 58, for example, as may be selected by menu tabs, buttons or the like as is well-known in the art. In this way confusion as to the identity of each flexible tube associated with a particular medicament may be quickly linked to data on the display 60.

Figure 7:
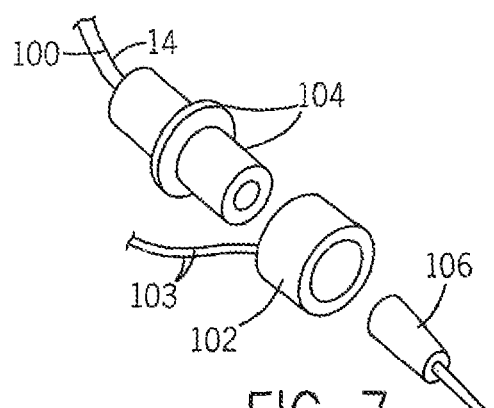
FIG. 7 is a fragmentary view of an end of the flexible tube showing a colored cap that may be installed on the flexible tube to provide either a static or electronically controlled marking of the needle associated with each pump unit.

Referring also to FIG. 7, alternatively it is contemplated that different flexible tubes 14 may be marked using different colors, with these colors optionally being those recorded in the pump module as color information 38*e* referenced on the display 60. The color marking may, for example, be colored flexible tubes 14 such as may be manufactured by co-extrusion of a colored plastic along with the flexible tube to provide a color stripe 100 or the introduction of a collar 102 over the luer-lock 104 of the flexible tube 14 to which the needle 106 is attached. In one embodiment, conductors 103 may extend along the flexible tube 14 (either externally or embedded in the flexible tube 14) so that the base station processor 52 may control a three-color LED capable of producing a variety of different hues within the color collar 102 for identification of the needle 106 itself to a particular pump module 10 and medicament.

Figure 5:
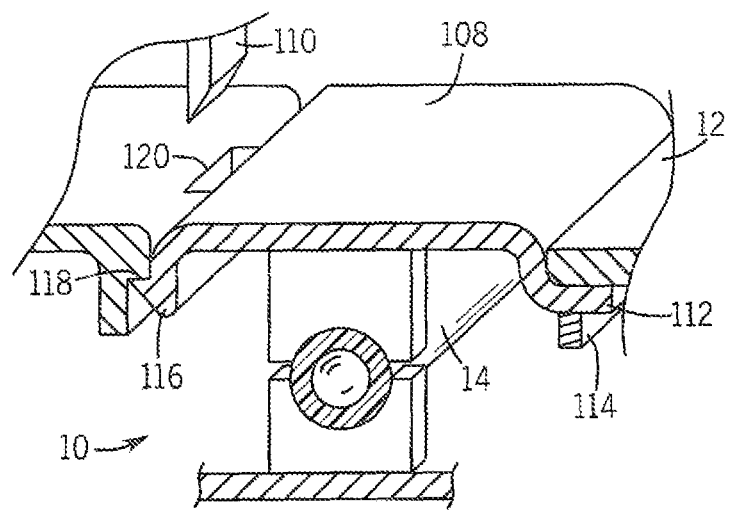
FIG. 5 is a cross-sectional, orthogonal view perpendicular to the axis of the flexible tube passing through a pump module showing a locking cover that can be removed with a tool.

Referring momentarily to FIG. 5, in addition or alternatively, a cover plate 108 fitting over the flexible tube 14 as it passes through the pump module 10 may be given a particular color recorded by the color information 38*e* in the pump module 10. This cover plate 108 may serve to retain the flexible tube in position within the housing 12 of the pump module 10 and may require a special tool 110 for removal. For example, the cover plate 108 may provide for tabs 112 on one side received within corresponding slots 114 in the housing 12 to provide a hinge connection with one side of the cover plate 108. The other side of the cover plate 108 may provide for a flexing barb 116 that may be captured on a ledge 118 within the housing 12 when the cover plate is pressed down over the flexible tube 14. Release of the barb 116 from the ledge 118 may be accomplished only with the insertion of a wedge tool 110 through an opening 120 that presses the barb 116 away from the ledge allowing release of the cover plate 108. In this way the flexible tubes 14 may be preinstalled in the pump modules 10 without concern for casual disconnection or a changing of particular pump modules 10 associated with particular IV kits 16.

Referring again to FIG. 8 after any color marking has been set, the base station 44 confirms drugs information 38*a* and dose information 38*b* (if present) as received from the pump modules 10 and as indicated by process block 128. This confirmation cheeks the information from each pump module 10 against independently obtained information 64 linking a particular patient to the proper drugs and dosages and thus ensuring that the patient is supposed to receive these drugs of the install pump modules 10 and has not already receive these drugs. At this time, the base station 44 may also check for interaction among the drugs in the pump modules 10 using a drug interaction database reference from the electronic medical record system 70.

It will be understood from this description that each of the components of the present modular pump can have specific pieces of information that are assembled together to ensure proper delivery of medicament to the patient, with the pump modules 10 holding information specific to a drug and the base station 44 holding billing information specific to a patient that helps coordinate and cheek on the drug information.

If there is a failure to confirm the proper drugs or dosage or any of the checks described above, the pump module 10 may be deactivated and an error code displayed on the display 60 and communicated through the wireless transceiver 56 with the electronic medical record system 70 to notify the proper personnel.

Referring still to FIG. 8, at process block 130 the patient may be confirmed, for example, by entry of the patient identification into data entry device 63 either manually through a keyboard or by scanning a patient's wristband or the like with a barcode scanner 133 shown in FIG. 2. This identification may be compared against the patient information used at process block 128 generating an error if there is no match. Alternatively process block 130 may occur before process block 128 so as to provide an index (the patient ID) used to obtain the necessary data from the electronic medical record system 70.

At this time, each of the flexible tubes 14 may be sequentially illuminated as relevant data is displayed on display 60 indicating, for example, the drug type and needle placement, and the operating personnel may confirm needles 106 through entry of confirming information through data entry device 63. Again if there is a failure to identify proper placement of the IV needles 106, operation of the pump module 10 may cease and notifications be transmitted.

Assuming that the patient information and drug information are compatible, program 88 enters into a drug delivery loop providing delivery of the medicaments by activating each of the pump modules 10 appropriately according to the schedule information 64*f* shown in FIG. 3. At this time all operation of the pump modules 10 is monitored by the base station processor 52, monitoring sensors 47 and optional sensors 41, and also monitoring operation of the motor 26, for example, by checking current consumption or other optional diagnostics, for example, rotation sensors, on the motor 26 and the like.

Assuming at decision block 134 that monitoring indicates proper operation and delivery of the medicament with conformance to the schedule information 64*f*, the pumping proceeds until it is complete and the program 88 proceeds to process block 136 where it logs the delivery of the medicament and communicates this delivery back to the electronic medical record system 70. In the event that there is an error during the delivery of the medicament, then as indicated by process block 138, the faulting pump module 10 is disabled and an alarm signal is sent to the electronic medical record system 70 and displayed on display 60 including a display at the pump module 10 showing the point of the error.

Referring now to FIG. 8, a program 140 executing in, the pump modules 10, upon receiving power from the base station 44, may wait at decision block 142 for a request for the information 38 from the base station 44 upon which request the requested information may be provided to the base station 44.

At decision block 144 the pump module 10 may wait for the activation command from the base station 44 occurring a process block 132 of the base station program. During this time the pump module 10 may report any error condition sensed by the pump module 10 to the base station 44. In a minimal embodiment, the pump module 10 programming may be extremely simple and therefore universal, with more sophisticated programming being incorporated into the base station 44 into which it may be downloaded from a database such as the drug dispense system, or electronic medical record system 70. In a more sophisticated embodiment, programming information may be downloaded from a database directly to the pump instead of downloading to the base station.

Upon receiving a cease operation signal from the base station 44 or detecting an error condition, the pump module 10 may proceed to process block 146 to log the information about the delivery of the medicament. Generally this information may be limited to the fact of the delivery.

Upon completion of this logging process, as indicated by process block 148, the pump module 10 locks itself to prevent reuse until it has received new programming and a new medicament. This reprogramming may be provided only after the provision of a password known, for example, by appropriate medical personnel and may be communicated through the communication interface 34 eliminating a need for conventional user interfaces such as switches or the like on the pump modules 10.

Process block. 148 may also evaluate the service life of the pump module 10 to irrevocably lock the pump module 10 once that service life is exceeded. This locking allows cost-efficient, lower service life components to be used safely, and a lock value may be stored in nonvolatile memory to prevent altering without disassembly of the pump and access to internal components. Service life may estimate the total fluid flow, for example, to set a service life of less than 100 liters or a total pumping time, for example, of less than 1000 hours.

It will be appreciated that the pump modules 10 may be extremely simple both in implementation and hardware and thus may be relatively inexpensive and for this reason may be pre-associated with inventoried medicaments to be readily available.

Figure 6:
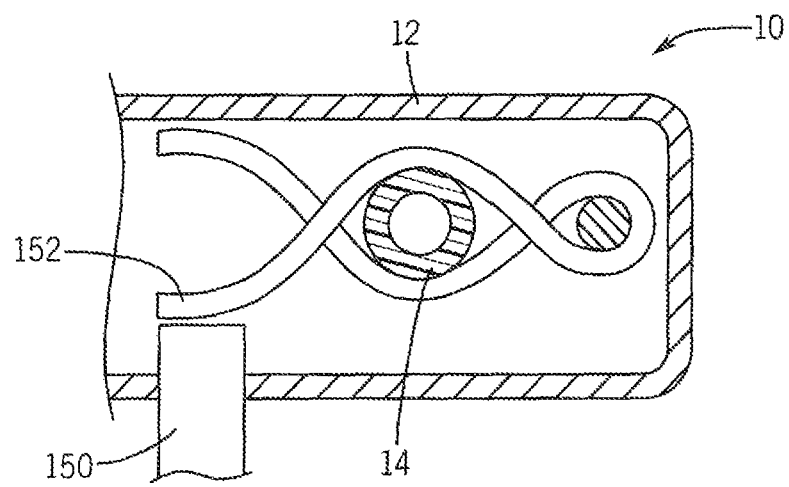
FIG. 6 is a cross-section view through the pump unit perpendicular to the axis of the flexible tube showing a mechanical clamp released only when the pump unit is placed in the receptacle of the base station.

Referring now to FIGS. 3 and 6, in one embodiment each socket 40 may have a key 150 extending into the socket 40 that may pass through an opening in the rear of the housing 12 of the pump module 10 to press on a spring-loaded clamp 152. The spring-loaded clamp 152 in a relaxed state not pressed by the key 150 compresses the flexible tube 14 to close the same. The flexible tube 14 is opened when the key 150 presses on the spring-loaded clamp 152. The clamp 152 ensures that fluid does not leak through the flexible tube prior to installation of the pump module 10 in each socket 40.

Referring now to FIG. 10, in an alternative embodiment, the housings 12 of the pump modules 10 may include syringe holding clips 154*a* and 154*b*, for example, constructed of a flexible polymer material attached, for example, on a front face of the cover plate 108 to support a syringe 156 preloaded with medicament. The syringe 156 may be held in vertical orientation parallel to axis 30 with a syringe plunger 159 downward and thus removed from interference and a leer lock 160 of the syringe 156 facing upward and attached to a short section of flexible tube 14 which may then loop downward through the pump module 10 as described above. The peristaltic pump action of the present invention uses multiple plungers that compress sequential portions of the IV tubing at different times, for example, providing three plungers operating with 120 degrees of phase difference in their reciprocation, and can pull medicament from a syringe 156 in lieu of a bag 18 as shown in FIG. 1 without the need for conventional and bulky mechanisms to retain the syringe 156 during compression of the syringe plunger 159.

Figure 12:
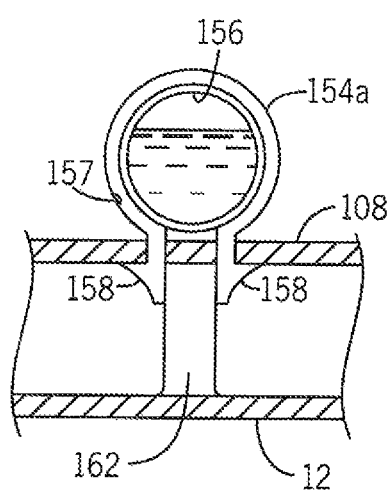
FIG. 12 is a cross-sectional view along line 12-12 of FIG. 10 showing one embodiment of a tamper-resistant syringe retention clip possible with the present invention.

Referring also to FIG. 12, in this embodiment, the syringe 156 may be preinstalled on the pump module 10 and one of the clips 154*a* may be tamper resistant. For example, clip 154*a* may be placed around the syringe 156 and barbed ends 158 of the clip 154 inserted through holes in the plate 108, the latter discussed above with respect to FIG. 5. The barbs on the barbed ends 158 of the clip 154*a* after being inserted through corresponding holes in the plate 108 flex outward to engage the underside of the plate 108 preventing removal of the clip 154*a* without compression inward of the barbed ends 158 toward each other moving the barbs away from their engagement with the undersurface of the plate 108. When the plate 108 is installed on the housing 12 of the pump module 10, inward movement of the barbed ends 158 may be blocked by a stop member 162 extending upward from the lower wall of the housing 12 in between the barbed ends 15$ of the clip 154*a* preventing removal of the clip 154*a* as long as the plate 108 is installed on the housing 12.

In this way the same locking mechanism that holds plate 108 in place may retain the syringe 156 against tampering, removal, and replacement.

The clip 154a may have a score 157 cutting partly through the wall of the clip such that if the syringe 156 is forcibly removed from the plate 108, the clip 154a brakes at the score 157 instead of causing the removal of the barbs 158. The natural resilience of the clip 154a then causes the clip 154a to open up and one of the barbs 158 to fail inside of the housing 12 clearly indicating its damage and preventing it from cosmetically holding the syringe 156.

Figure 11:
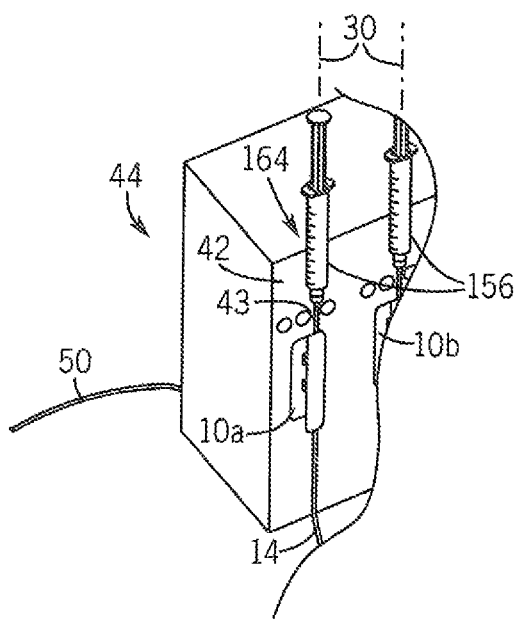
FIG. 11 is a fragmentary view similar to that of FIG. 2 showing an alternative arrangement in which mounting for a syringe is contained on the base station.

Referring now to FIG. 11, in an alternative embodiment, the front faceplate 42 of the base station 44 may provide for retention slots 164, for example, having elastomeric fingers that receive and retain syringes 156 in alignment along axes 30 and channels 43. As so positioned, the syringes 156 may communicate with different corresponding pump modules 10a and 10b replacing the need for IV bags 18 and bag support structure.

Figure 13:
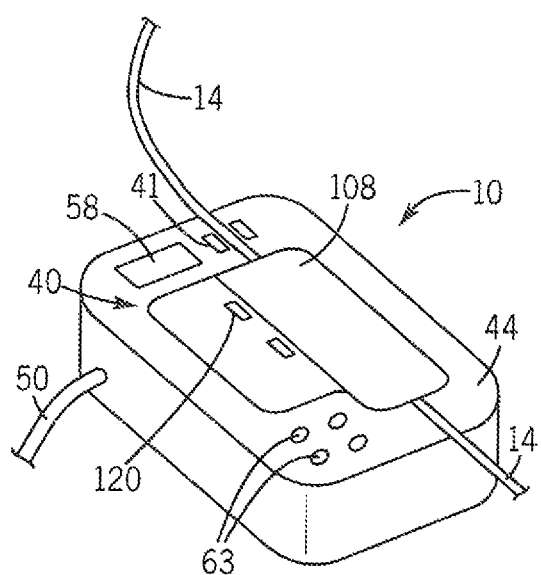
FIG. 13 is a perspective view of a pump unit installed in a single receptacle base unit, for example, for home health care use.

Referring now to FIG. 13, the pump module 10 may fit in a base station 44 having a single socket 40, for example, sized to fit on a side table or the like or to be mounted on an IV pole as shown, for example, in FIG. 2. In all other respects, the base station 44 and pump module 10 may be as described in any of the embodiments discussed above.

Certain terminology is used herein for purposes of reference only, and thus is not intended to be limiting. For example, terms such as "upper", "lower", "above", and "below" refer to directions in the drawings to which reference is made. Terms such as "front", "back", "rear", "bottom" and "side", describe the orientation of portions of the component within a consistent but arbitrary frame of reference which is made clear by reference to the text and the associated drawings describing the component under discussion. Such terminology may include the words specifically mentioned above, derivatives thereof, and words of similar import. Similarly, the terms "first", "second" and other such numerical terms referring to structures do not imply a sequence or order unless clearly indicated by the context. Indication is used herein to mean any type of sense to indication including an audio alarm, visual display or other computer-controlled activation (motor buzz, etc.)

When introducing elements or features of the present disclosure and the exemplary embodiments, the articles "a", "an", "the" and "said" are intended to mean that there are one or more of such elements or features. The terms "comprising", "including" and "having" are intended to be inclusive and mean that there may be additional elements or features other than those specifically noted. It is further to be understood that the method steps, processes, and operations described herein are not to be construed as necessarily requiring their performance in the particular order discussed or illustrated, unless specifically identified as an order of performance. It is also to be understood that additional or alternative steps may be employed.

References to "a microprocessor" and "a processor" or "the microprocessor" and "the processor," can be understood to include one or more microprocessors or other types of computers, gate arrays or the like that can execute programs and communicate with each other. Furthermore, references to memory, unless otherwise specified, can include one or more processor-readable and accessible memory elements and/or components that can be internal to the processor-controlled device, external to the processor-controlled device, and can be accessed via a wired or wireless network. The term manual pushbuttons means buttons that may be operated by finger touch or the like including touchscreen and passive switch and mechanical switch.

It is specifically intended that the present invention not be limited to the embodiments and illustrations contained herein and the claims should be understood to include modified forms of those embodiments including portions of the embodiments and combinations of elements of different embodiments as come within the scope of the following claims. All of the publications described herein, including patents and non-patent publications are hereby incorporated herein by reference in their entireties.

We claim:

1. A modular medical pump system for a drug kit having a flexible delivery tube from a drug container, the modular medical pump system comprising:
    a controller including:
        (a) an electronic processor holding a first stored program for execution by the electronic processor; and
        (b) a programming station interface for releasably receiving a pump unit for communication of control information to the pump unit as so received based on the execution of the first stored program; and
    at least one pump unit releasably receivable by a connector of the controller, the at least one pump unit including:
        (a) a housing carried by the delivery tube extending therethrough, the housing including a retention element locking at least one of the delivery tube and the drug container to the housing of the pump unit against unauthorized removal;
        (b) an electromechanical pump held by the housing and communicating with the delivery tube in the housing to pump fluid through the delivery tube;
        (c) a pump unit electronic processor held by the housing and communicating with the electromechanical pump and holding a second stored program holding drug information indicating a drug identity and a data log for logging actual delivery of medicament to a patient including an amount delivered and a date of delivery between receiving an activation command and a cease operation signal from the controller; and
        (d) a secure pump unit communications interface within the housing and adapted to be inaccessible by a patient proximate to the housing and exclusive of pushbutton controls exposed at an exterior of the housing, the secure pump unit communication interface receiving the control information from the controller for control of the electromechanical pump when the pump unit is received by the controller;
    wherein the pump unit electronic processor prevents operation of the electromechanical pump after receiving the cease operation signal until new drug information indicating new drug identity and new control information are received by the processor together with a predetermined password; and
    wherein the retention element is adapted to require an unlocking tool to remove the drug kit from the housing.

2. The modular medical pump system of claim 1 wherein the drug container remains external to the housing.

3. The modular medical pump system of claim 1 wherein the pump unit is sized and adapted to be fully supported on the drug kit when the drug kit is transported.

4. The modular medical pump system of claim 1 wherein the retention element provides a tamper feature indicating attempted unauthorized removal of the drug kit from the housing.

5. The modular medical pump system of claim 1 wherein the controller further provides a source of electrical power to the pump unit when the pump unit is received by the controller.

6. The modular medical pump system of claim 1 wherein the controller further includes a wireless transceiver for communicating with a remote medical database.

7. The modular medical pump system of claim 1 wherein the controller includes guides for receiving the delivery tube and wherein the guides include proximate sensors for sensing at least one of: a flow rate through the delivery tube, air bubbles in the delivery tube, and a pressure in the delivery tube.

8. The modular medical pump system of claim 1 wherein each pump unit includes a mechanical delivery tube clamp closing the delivery tube against flow that is released when the pump unit is received by the controller.

9. The modular medical pump system of claim 1 further including a syringe engaging structure for holding a drug container and preventing non-damaging manual removal of the drug container from the pump unit after so attached without use of an unlocking tool.

10. The modular medical pump system of claim 1 wherein the controller includes multiple connectors for releasably receiving multiple pump units, each connector providing a receptacle for receiving and supporting the housing of the pump unit.

11. The modular medical pump system of claim 10 wherein the controller includes guides for receiving and retaining delivery tubes attached to pump units and wherein the guides include proximate sensors for sensing at least one of: a flow rate through the delivery tube, air bubbles in the delivery tube, and a pressure in the delivery tube.

12. The modular medical pump system of claim 10 wherein each connector includes a wireless charging circuit providing electrical power to a received pump unit by electromagnetic transmission, and wherein the pump units do not contain power storage sufficient for operation of the pump unit for delivery of a drug treatment course.

13. The modular medical pump system of claim 10 wherein the housing of the pump units includes a replaceable drug identification indicium.

14. The modular medical pump system of claim 10 wherein the control information is communicated wirelessly between the controller and the pump unit.

15. The modular medical pump system of claim 10 wherein the controller includes an electronic data input interface for identifying a patient.

16. The modular medical pump system of claim 10 wherein the controller includes mountings holding the controller on an IV pole.

17. The modular medical pump system of claim 10 further including a human-perceivable indicium unique to and proximate to each delivery tube of an associated installed pump unit marking the delivery tubes for a separate identification.

18. The modular medical pump system of claim 17 wherein the human-perceivable indicium are electronically controlled to be changed according to the pump units installed in the controller.

19. The modular medical pump system of claim 18 providing an electronic display and operating to switch between displaying information from different pump units while simultaneously indicating the pump unit from which information is displayed by means of the human-perceivable indicium proximate to the delivery tubes of the pump units.

20. The modular medical pump system of claim 18 wherein the human-perceivable indicium provides an illumination of the delivery tube according to the pump units installed in the controller.

21. The modular medical pump system of claim 1 wherein the housing includes vertical channels receiving the delivery tube therethrough.

22. A modular medical pumping system, the modular medical pump system comprising:

a main controller including:
 (a) an electronic processor holding a first stored program for execution by the electronic processor; and
 (b) a programming station interface for releasably receiving a pump unit for communication of control information to the pump unit as so received based on the execution of the first stored program; and at least one pump unit releasably receivable by a connector of the controller, the at least one pump unit including:
 (a) a housing carried by a delivery tube extending therethrough;
 (b) an electromechanical pump held by the housing and communicating with the delivery tube in the housing to pump fluid through the delivery tube;
 (c) a pump unit electronic processor held by the housing and communicating with the electromechanical pump and holding a second stored program holding drug information indicating a drug identity and a data log for logging actual delivery of medicament to a patient including an amount delivered and a date of delivery between receiving an activation command and a cease operation signal from the controller; and
 (d) a secure pump unit communications interface within the housing and adapted to be inaccessible by a patient proximate to the housing and exclusive of pushbutton controls exposed at an exterior of the housing, the secure pump unit communication interface receiving the control information from the main controller for control of the electromechanical pump when the pump unit is received by the controller;

wherein the pump unit electronic processor prevents operation of the electromechanical pump after receiving the cease operation signal until new drug information indicating new drug identity and new control information are received by the processor together with a predetermined password; and wherein the retention element is adapted to require an unlocking tool to remove the drug kit from the housing.

23. The modular medical pump system of claim 1 wherein the second stored program further holding drug dose information including a drug amount and a drug delivery flow rate.

* * * * *